(12) United States Patent
Malkowski

(10) Patent No.: US 10,881,391 B2
(45) Date of Patent: Jan. 5, 2021

(54) SEALING PACK ASSEMBLY FOR USE WITH ENDOSCOPIC STITCHING DEVICE

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 182 days.

(21) Appl. No.: 16/120,539

(22) Filed: Sep. 4, 2018

(65) Prior Publication Data

US 2019/0133570 A1    May 9, 2019

Related U.S. Application Data

(60) Provisional application No. 62/581,115, filed on Nov. 3, 2017.

(51) Int. Cl.
*A61B 17/04*     (2006.01)
*A61B 17/062*    (2006.01)
*A61B 17/29*     (2006.01)

(52) U.S. Cl.
CPC ...... *A61B 17/0469* (2013.01); *A61B 17/0625* (2013.01); *A61B 2017/0472* (2013.01); *A61B 2017/2939* (2013.01); *A61B 2017/2948* (2013.01)

(58) Field of Classification Search
CPC . A61B 17/0469; A61B 17/0625; A61B 17/29; A61B 2017/0472; A61B 2017/2939; A61B 2017/2948
See application file for complete search history.

(56) References Cited

U.S. PATENT DOCUMENTS

| | | | |
|---|---|---|---|
| 1,037,864 A | 9/1912 | Carlson et al. |
| 1,131,163 A | 3/1915 | Saunders et al. |
| 1,293,565 A | 2/1919 | Smit |
| 1,449,087 A | 3/1923 | Bugbee |
| 1,876,792 A | 9/1932 | Thompson |
| 2,213,830 A | 9/1940 | Anastasi |
| 2,880,728 A | 4/1959 | Rights |
| 3,090,386 A | 5/1963 | Curtis |
| 3,349,772 A | 10/1967 | Rygg |

(Continued)

OTHER PUBLICATIONS

International Search Report and Written Opinion issued in International Application No. PCT/US2018/057911, dated Jul. 12, 2019.

*Primary Examiner* — Ashley L Fishback
(74) *Attorney, Agent, or Firm* — Carter DeLuca & Farrell LLP

(57) ABSTRACT

An endoscopic stitching device includes an elongate shaft assembly, a tool assembly coupled with the elongate shaft assembly, and a sealing pack disposed in the elongate shaft assembly. The sealing pack defines a central lumen configured to receive an axial rod therethrough, and first and second lumens dimensioned to receive respective first and second needle receiving blades therethrough. The sealing pack includes a body portion, a plurality of outer lips extending outwardly from the body portion, and a plurality of inner lips extending inwardly from the central lumen. Each outer lip of the plurality of outer lips is configured to engage the elongate shaft assembly in a sealing relation. Each inner lip of the plurality of inner lips is configured to engage the axial rod in a sealing relation.

23 Claims, 4 Drawing Sheets

(56) References Cited

U.S. PATENT DOCUMENTS

| | | |
|---|---|---|
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |
| 3,946,740 A | 3/1976 | Bassett |
| 4,021,896 A | 5/1977 | Stierlein |
| 4,109,658 A | 8/1978 | Hughes |
| 4,161,951 A | 7/1979 | Scanlan, Jr. |
| 4,164,225 A | 8/1979 | Johnson et al. |
| 4,236,470 A | 12/1980 | Stenson |
| 4,345,601 A | 8/1982 | Fukuda |
| 4,373,530 A | 2/1983 | Kilejian |
| 4,471,781 A | 9/1984 | Di Giovanni et al. |
| 4,491,135 A | 1/1985 | Klein |
| 4,580,567 A | 4/1986 | Schweitzer et al. |
| 4,621,640 A | 11/1986 | Mulhollan et al. |
| 4,635,638 A | 1/1987 | Weintraub et al. |
| 4,890,615 A | 1/1990 | Caspari et al. |
| 4,923,461 A | 5/1990 | Caspari et al. |
| 4,935,027 A | 6/1990 | Yoon |
| 4,957,498 A | 9/1990 | Caspari et al. |
| 5,059,201 A | 10/1991 | Asnis |
| 5,100,421 A | 3/1992 | Christoudias |
| 5,171,257 A | 12/1992 | Ferzli |
| 5,181,919 A | 1/1993 | Bergman et al. |
| 5,207,693 A | 5/1993 | Phillips |
| 5,217,471 A | 6/1993 | Burkhart |
| 5,242,458 A | 9/1993 | Bendel et al. |
| 5,254,126 A | 10/1993 | Filipi et al. |
| 5,261,917 A | 11/1993 | Hasson et al. |
| 5,281,220 A | 1/1994 | Blake, III |
| 5,336,230 A | 8/1994 | Leichtling et al. |
| 5,454,823 A | 10/1995 | Richardson et al. |
| 5,674,229 A | 10/1997 | Tovey et al. |
| 5,674,230 A * | 10/1997 | Tovey ............... A61B 17/0469 606/139 |
| 5,766,167 A | 6/1998 | Eggers et al. |
| 5,980,538 A | 11/1999 | Fuchs et al. |
| 6,270,508 B1 | 8/2001 | Klieman et al. |
| 7,824,401 B2 | 11/2010 | Manzo et al. |
| 8,177,794 B2 | 5/2012 | Cabrera et al. |
| 8,226,667 B2 | 7/2012 | Viola et al. |
| 8,246,637 B2 | 8/2012 | Viola et al. |
| 8,292,905 B2 | 10/2012 | Taylor et al. |
| 8,292,906 B2 | 10/2012 | Taylor et al. |
| 8,337,515 B2 | 12/2012 | Viola et al. |
| 8,372,090 B2 | 2/2013 | Wingardner et al. |
| 8,454,631 B2 | 6/2013 | Viola et al. |
| 8,460,275 B2 | 6/2013 | Taylor et al. |
| 8,490,713 B2 | 7/2013 | Furnish et al. |
| 8,496,674 B2 | 7/2013 | Cabrera et al. |
| 8,506,581 B2 | 8/2013 | Wingardner, III et al. |
| 8,628,545 B2 | 1/2014 | Cabrera et al. |
| 8,636,752 B2 | 1/2014 | Cabrera et al. |
| 8,747,424 B2 | 6/2014 | Taylor et al. |
| D708,746 S | 7/2014 | Cabrera et al. |
| 8,864,776 B2 | 10/2014 | Bogart et al. |
| 8,968,340 B2 | 3/2015 | Chowaniec et al. |
| 8,968,342 B2 | 3/2015 | Wingardner, III et al. |
| 9,113,860 B2 | 8/2015 | Viola et al. |
| 9,271,723 B2 | 3/2016 | Taylor et al. |
| 9,615,824 B2 | 4/2017 | Furnish et al. |
| 9,675,340 B2 | 6/2017 | Sniffin et al. |
| 2004/0260314 A1 | 12/2004 | Lizardi |
| 2005/0149066 A1 | 7/2005 | Stafford |
| 2006/0020274 A1 | 1/2006 | Ewers |
| 2009/0221868 A1 | 9/2009 | Evans |
| 2009/0299406 A1 | 12/2009 | Swain |
| 2010/0016852 A1 | 1/2010 | Manzo et al. |
| 2010/0228270 A1 | 9/2010 | Bogart et al. |
| 2011/0040308 A1 | 2/2011 | Cabrera et al. |
| 2013/0023725 A1 | 1/2013 | Nose |
| 2013/0096498 A1 | 4/2013 | Baur et al. |
| 2015/0327850 A1 | 11/2015 | Kostrzewski |

\* cited by examiner

SEALING PACK ASSEMBLY FOR USE WITH ENDOSCOPIC STITCHING DEVICE

CROSS-REFERENCE TO RELATED APPLICATION

This application claims the benefit of and priority to U.S. Provisional Patent Application No. 62/581,115 filed Nov. 3, 2017, the entire disclosure of which is incorporated by reference herein.

BACKGROUND

Technical Field

The present disclosure relates to devices for use with suturing or stitching and, more particularly, to a sealing pack assembly on devices for endoscopic suturing or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. In such surgical procedures, it is necessary to manipulate a surgical needle, having a length of suture material attached thereto, with a surgical stitching device. In such a stitching device, it is desirable to inhibit fluids from entering into a distal end of an elongate shaft assembly of the stitching device. Therefore, a need exists for simple and effective devices capable of inhibiting passage of fluids into a distal end of the stitching device.

SUMMARY

The present disclosure describes a sealing pack assembly that demonstrates a practical approach to meeting the performance requirements and overcoming usability challenges associated with keeping fluids from entering into a distal end of an elongate shaft assembly of a surgical stitching device. In accordance with an embodiment of the present disclosure, an endoscopic stitching device includes an elongate shaft assembly, a tool assembly, and a sealing pack. The elongate shaft assembly includes an axial rod extending therethrough. The tool assembly is coupled with the elongate shaft assembly. The tool assembly includes first and second jaws operatively coupled with the axial rod of the elongate shaft assembly such that axial displacement of the axial rod transitions the first and second jaws between open and closed positions. First and second needle receiving blades are slidably disposed in the respective first and second jaws. The sealing pack is disposed in the elongate shaft assembly to inhibit passage of fluid into the elongate shaft assembly. The sealing pack defines a central lumen configured to receive the axial rod therethrough, and first and second lumens dimensioned to receive the respective first and second needle receiving blades therethrough. The sealing pack includes a body portion, a plurality of outer lips extending outwardly from the body portion, and a plurality of inner lips extending inwardly from the central lumen. Each outer lip of the plurality of outer lips is configured to engage the elongate shaft assembly in a sealing relation. Each inner lip of the plurality of inner lips is configured to engage the axial rod in a sealing relation.

In an embodiment, the endoscopic stitching device may further include a plurality of sealing packs. The plurality of sealing packs may be formed as a single construct.

In another embodiment, the axial rod may include opposing planar surfaces. Each inner lip of the plurality of inner lips may include planar surfaces configured to engage the respective opposing planar surfaces of the axial rod.

In yet another embodiment, the elongate shaft assembly may further include a clevis including a base and a pair of legs. The base may define a central aperture in communication with the central lumen of the sealing pack.

In still another embodiment, the clevis may define third and fourth lumens in communication with the respective first and second lumens of the sealing pack.

In still yet another embodiment, the sealing pack may be connected to the clevis.

In still yet another embodiment, the inner lips may be spaced apart along a longitudinal axis defined by the elongate shaft assembly and may be in registration with each other.

In accordance with another embodiment of the present disclosure, a tool assembly for use with an endoscopic stitching device is provided. The tool assembly includes a support member, first and second jaws, first and second needle receiving blades, and a sealing pack. The first and second jaws are operatively coupled with the support member to transition between open and closed positions. The first and second needle receiving blades are slidably received in the respective first and second jaws. The sealing pack is disposed within the support member to inhibit passage of fluid through the support member. The sealing pack defines a central lumen configured to receive an axial rod therethrough, and first and second lumens dimensioned to receive the respective first and second needle receiving blades therethrough. The sealing pack includes a body portion, a plurality of outer lips extending outwardly from the body portion, and a plurality of inner lips extending inwardly from the central lumen. Each outer lip of the plurality of outer lips is configured to engage the elongate shaft assembly in a sealing relation. Each inner lip of the plurality of inner lips is configured to engage the axial rod in a sealing relation.

In an embodiment, at least one outer lip of the plurality of outer lips may be formed of a compressible material.

In another embodiment, at least one inner lip of the plurality of inner lips and at least one outer lip of the plurality of outer lips may be formed as a single construct.

DETAILED DESCRIPTION OF THE DRAWINGS

The foregoing objects, features and advantages of the disclosure will become more apparent from a reading of the following description in connection with the accompanying drawings, in which.

DETAILED DESCRIPTION

Figure 1:
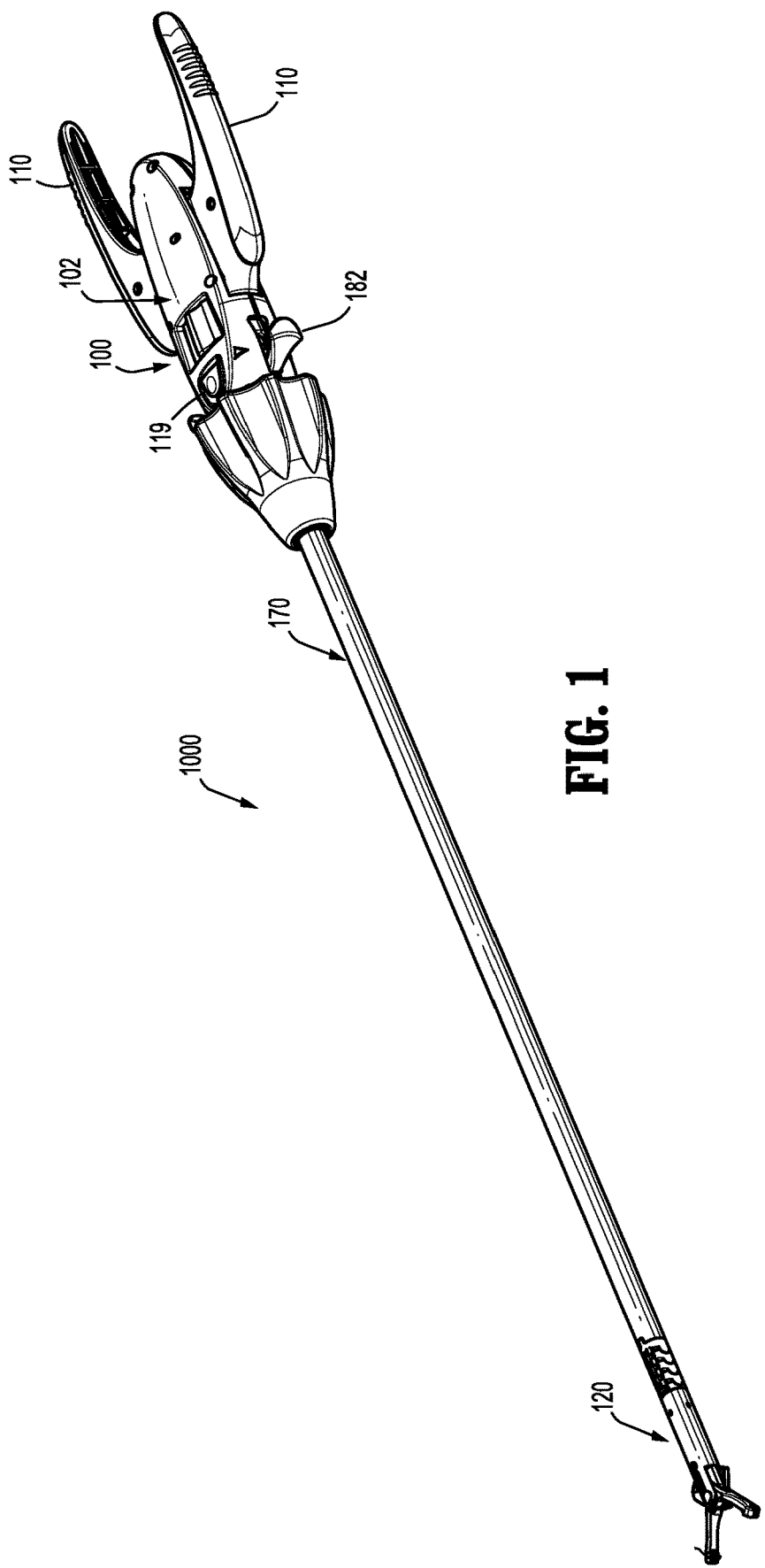
FIG. 1 is a perspective view of a surgical stitching device in accordance with an embodiment of the present disclosure.

Embodiments of the present stitching devices will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, an embodiment of the present disclosure is generally shown as a stitching device 1000. Stitching device 1000 is adapted to be particularly useful in endoscopic or laparascopic procedures, wherein an endoscopic portion of stitching device 1000 such as, e.g., a tool assembly 120, is insertable into an operative site, via a cannula assembly or the like (not shown). Stitching device 1000 includes a handle assembly 100, an elongate shaft assembly 170 extending distally from handle assembly 100, and tool assembly 120 detachably supported on a distal end of elongate shaft assembly 170. Such a configuration facilitates, e.g., sterilization of stitching device 1000 and loading of needle on tool assembly 120.

Figure 2:
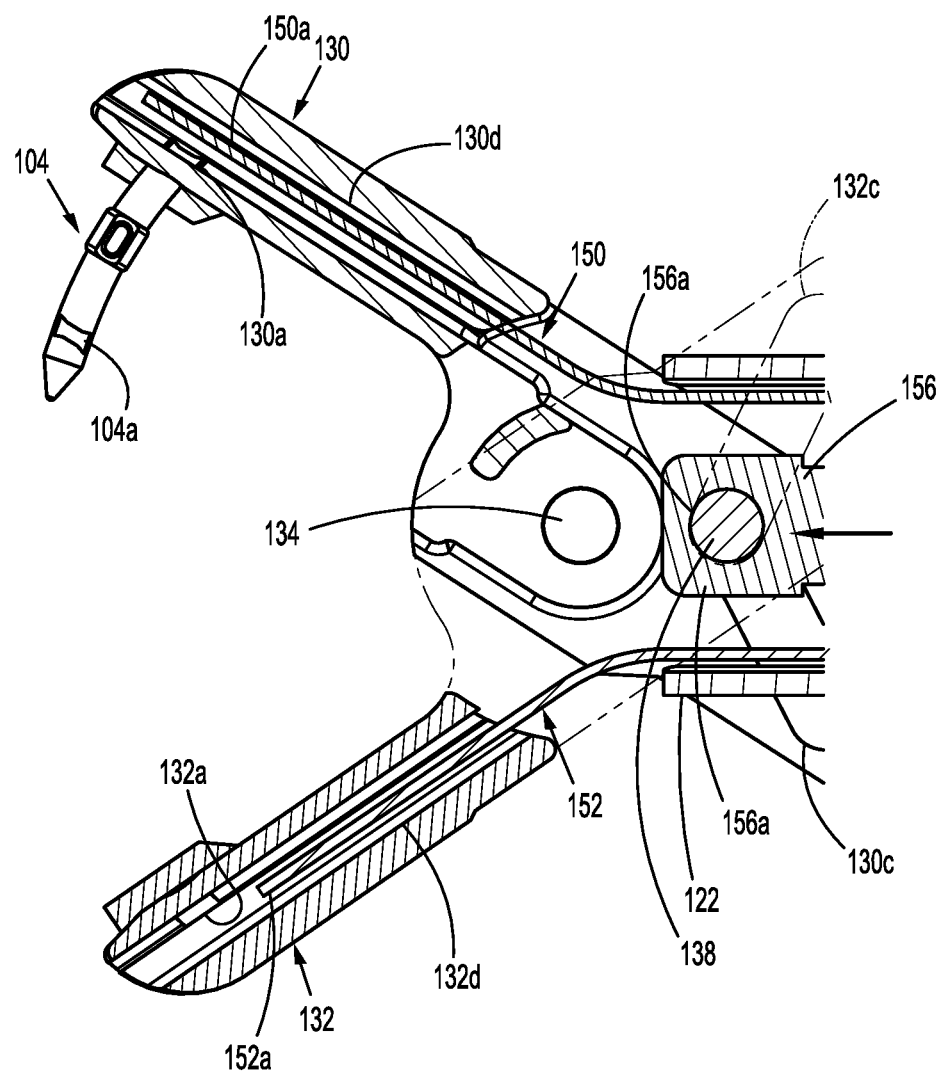
FIG. 2 is a partial cross-sectional view of a tool assembly of the surgical stitching device of FIG. 1.

With reference to FIGS. 1 and 2, tool assembly 120 includes a support member 122 and jaws 130, 132 pivotably mounted on support member 122 by means of a jaw pivot pin 134. To move jaws 130, 132 between an open position and a closed position, an axial rod 156 has a camming pin 138 mounted at a distal end 156a thereof. Camming pin 138 rides in angled camming slots 130c, 132c defined in respective jaws 130, 132 such that axial or longitudinal movement of axial rod 156 causes jaws 130, 132 to be cammed between the open and closed positions.

Figure 4:
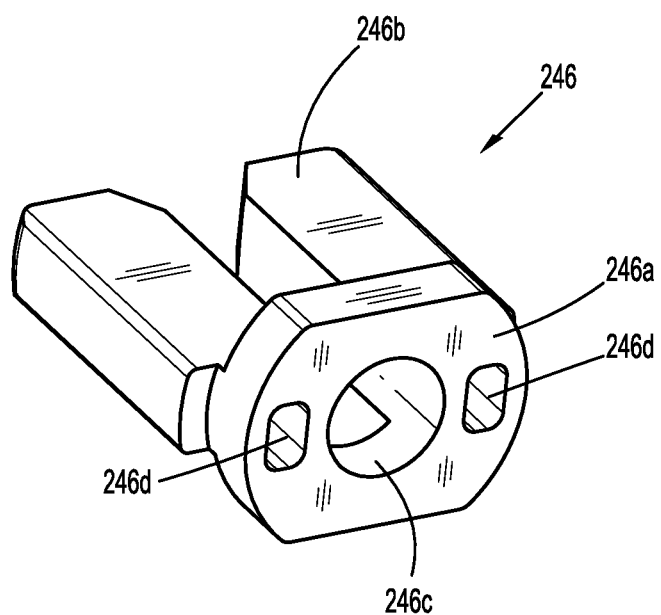
FIG. 4 is a perspective view of a clevis of FIG. 3.

Tool assembly 120 further includes a pair of needle engaging members or blades 150, 152 which are slidably supported within support member 122 by a clevis 246 (FIG. 4). Each blade 150, 152 includes a distal end 150a, 152a slidably extending into blade receiving channels 130d, 132d of respective jaws 130, 132. Channels 130d, 132d are dimensioned to at least partially intersect respective needle recesses 130a, 132a. Thus, by advancing blade 150 or 152 within respective channel 130d, 132d, distal end 150a, 152a of advancing blade 150, 152 engages or "locks in" a groove 104a formed in needle 104 when at least a portion of needle 104 is received within respective needle recesses 130a, 132a. A suture (not shown) is connected to needle 104.

Suture 2080 may include a plurality of barbs oriented to resist movement in a direction opposite to the direction of travel.

With continued reference to FIGS. 1 and 2, handle assembly 100 includes a pair of handles 110 pivotably secured to housing 102. Handles 110 are operatively coupled to axial rod 156 such that when handles 110 are squeezed, axial rod 156 is displaced proximally. Axial rod 156 may be provided with, e.g., a biasing member (not shown), in the form of a return spring, to bias axial rod 156 to an initial position. Axial rod 156 is operatively coupled to jaws 130, 132 of tool assembly 120, such that axial displacement of axial rod 156 transitions jaws 130, 132 between the open and closed positions.

With particular reference to FIG. 1, handle assembly 100 further includes a lever 182 pivotably supported in housing 102 and extending transversely from housing 102. Lever 182 is operatively coupled to blades 150, 152 (FIG. 2) of tool assembly 120. Lever 182 may be pivoted to cause reciprocating axial displacement of blades 150, 152 to enable swapping of needle 104 between jaws 130, 132.

With continued reference to FIG. 1, handle assembly 100 further includes a slider 119 (FIG. 1) operatively coupled with lever 182 to slide lever 182 distally to transition handle assembly 100 to a reload mode. In the reload mode, both blades 150, 152 (FIG. 2) are in a distal-most position. In this manner, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 104 (FIG. 2) may be positioned or loaded into a selected one needle recess 130a, 132a of jaws 130, 132. Reference may be made to U.S. Pat. No. 8,628,545, entitled "Endoscopic Stitching Devices," the entire content of which is incorporated herein by reference, for a detailed discussed of the construction and operation of a handle assembly and a tool assembly.

Figure 3:
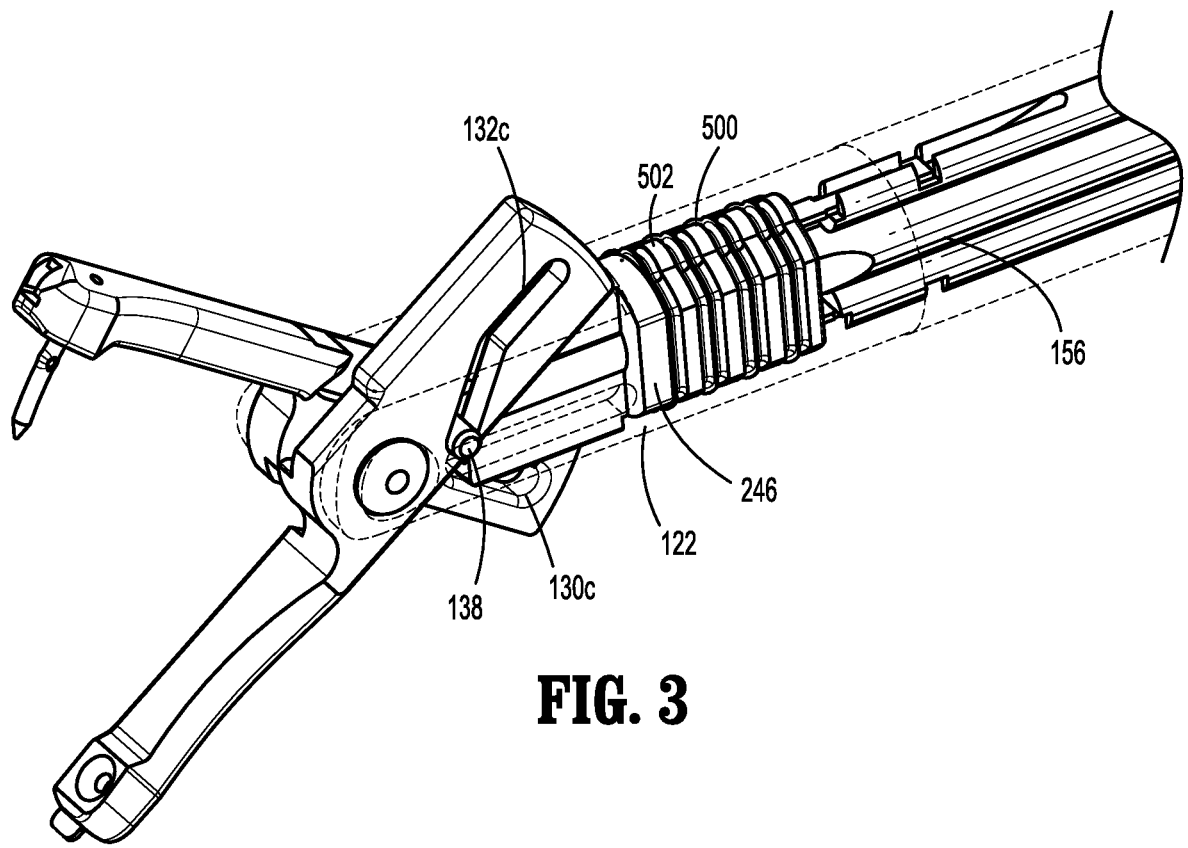
FIG. 3 is a partial perspective view of the stitching device of FIG. 1 illustrating a sealing pack assembly disposed in an elongate shaft assembly.

With reference now to FIGS. 3 and 4, clevis 246 is disposed in support member 122 and is configured to support blades 150, 152 (FIG. 2) and axial rod 156 in support member 122. Clevis 246 includes a base 246a and a pair of spaced apart arms 246b extending from base 246a. Base 246a defines first and second lumens 246d, and each arm 246b defines a lumen (not explicitly shown) in communication with respective first and second lumens 246d defined in base 246a. Base 246a further defines a central aperture 246c extending therethrough. Central aperture 246c is dimensioned to slidably receive axial rod 156 therethrough. Blades 150, 152 (FIG. 2) are configured to be slidably received through respective first and second lumens 246d of base 246a and the respective lumens of arms 246b. Blades 150, 152 slidably extend through clevis 246 and into blade receiving channels 130d, 132d of respective jaws 130, 132.

With continued reference to FIG. 3, support member 122 further includes a sealing pack assembly 500 configured to inhibit fluids from entering into a distal end of elongate shaft assembly 170. Sealing pack assembly 500 includes a plurality of sealing packs 502. Each sealing pack 502 may be formed of a compressible material such as, e.g., rubber, polymer, gel, foam or combinations thereof.

Figure 5:
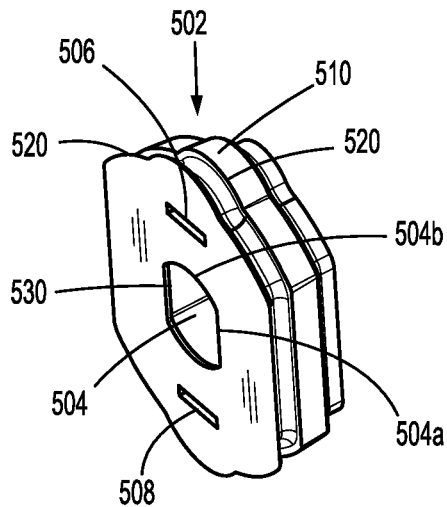
FIG. 5 is a perspective view of a single sealing pack of a sealing pack assembly of FIG. 3.
Figure 6:
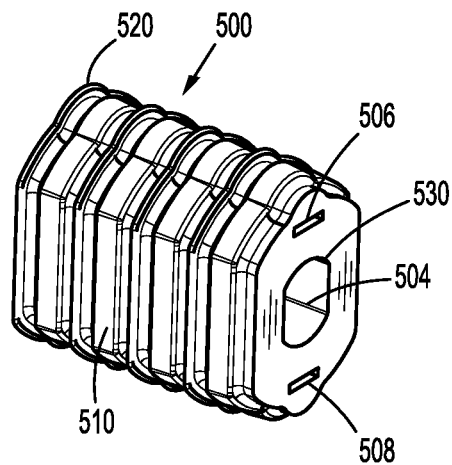
FIG. 6 is a perspective view of the sealing pack assembly of FIG. 3.
Figure 7:
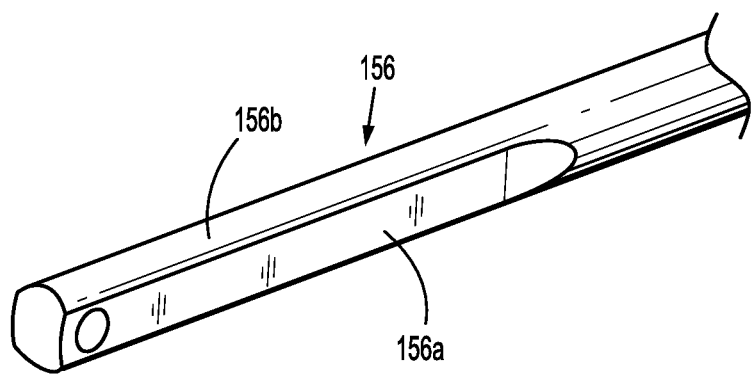
FIG. 7 is a perspective view of an axial rod of the stitching device of FIG. 3.

With reference to FIGS. 5-7, each sealing pack 502 has a substantially planar configuration defining a substantially hexagonal outer profile. Each sealing pack 502 defines a central lumen 504 dimensioned to receive axial rod 156 in a sealing relation therewith, and first and second lumens 506, 508 dimensioned to slidably receive blades 150, 152 therethrough in a sealing relation therewith. Central lumen 504 is in communication with central aperture 246c (FIG. 4) of clevis 246, and first and second lumens 506, 508 are in communication with first and second lumens 246d of clevis 246. Central lumen 504 includes opposing planar portions 504a configured to engage respective planar portions 156a of axial rod 156, and opposing arcuate portions 504b configured to engage respective arcuate portions 156b of axial rod 156. Sealing pack assembly 500 includes four sealing packs 502 stacked together. However, sealing pack assembly 500 may include any number of sealing packs 502, as needed, to meet the requirements of each stitching device such as, e.g., the leakdown test. Sealing packs 502 may be stacked individually within support member 122 such that each sealing pack 502 is frictionally supported within support member 122. Alternatively, sealing pack assembly 500 may be integrally formed as a single construct to enhance alignment of sealing packs 502. Further still, sealing pack assembly 500 may be attached to clevis 246 to enhance securement of sealing pack assembly 500 within support member 122.

Each sealing pack 502 includes a body portion 510, a plurality of outer lips 520 extending outwardly from body portion 510, and a plurality of inner lips 530 extending inwardly from central lumen 504. Outer lips 520 are continuous and extend around an entire perimeter of body portion 510. Similarly, inner lips 530 are continuous and extend around an entire perimeter of central lumen 504. Outer lips 520 are spaced apart along a longitudinal axis defined by support member 122 and are in registration with each other to provide multiple layers of seals. Similarly, inner lips 530 are spaced apart along the longitudinal axis of support member 122 and are in registration with each other to provide multiple layers of seals. Under such a configuration, the plurality of outer lips 520 engages the support member 122 in a sealing relation, and the plurality of inner lips 520 engages axial rod 156 slidably extending therethrough in a sealing relation (e.g., fluid tight sealing relation). An outer lip 520 and an inner lip 530 may be formed as a single construct such as, e.g., a single layer.

Sealing pack assembly 500 is pre-assembled in elongate shaft assembly 170 prior to use. In use, stitching device 1000 is first transitioned to the reload mode by sliding slider 119 (FIG. 1) distally such that both blades 150, 152 (FIG. 2) are in the distal-most position. In this manner, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 104 (FIG. 2) may be positioned or loaded into a selected one needle recess 130a, 132a of jaws 130, 132.

At this time, handles 110 (FIG. 1) may be squeezed to close jaws 130, 132. Once needle 104 is loaded or at least partially inserted into needle recesses 130a, 132a of jaws 130, 132, the notches (not shown) of blades 150, 152 are in registration with respective grooves 104a of needle 104. With needle 104 positioned such that the notches of blades 150, 152 are in registration with needle recesses 130a, 130b, lever 182 is actuated or rotated so that only one blade 150, 152 is moved into engagement with needle 104 (FIG. 2) to hold needle 104, and the other blade 150, 152 is disengaged from needle 104. With only one blade 150, 152 engaged with needle 104, handles 110 may be released, thereby moving axial rod 156 distally to open jaws 130, 132.

With jaws 130, 132 in the open position and needle 104 loaded and held in jaw 130 or 132, jaws 130, 132 may be positioned about or over a target tissue and handles 110 may be actuated to approximate jaws 130, 132. As jaws 130, 132 are approximated, the exposed end of needle 104 is penetrated through the target tissue and enters opposed jaw 130 or 132. With needle 104 in opposed jaw 130 or 132, lever 182 is once again actuated or rotated so that blades 150, 152 are reversed. In so doing, needle 104 is swapped from one blade 150 or 152 to the other blade 150 or 152, and thus, loaded or held in the other jaw 130 or 132.

With needle 104 being swapped from one blade 150, 152 to another blade 150, 152, handles 110 may be released to thereby open jaws 130, 132 and draw needle 104 through the target tissue. In so doing, a suture is also drawn through the tissue. The process is repeated, passing needle 104 between jaws 130, 132 and drawing the suture through the target tissue, thereby suturing the target tissue as needed or desired. In this manner, suturing process is effected, while inhibiting fluids from entering into a distal end of elongate shaft assembly 170.

Although the illustrative embodiments of the present stitching devices have been described herein with reference to the accompanying drawings, the above description, disclosure, and figures should not be construed as limiting, but merely as exemplifications of particular embodiments. For example, each sealing pack 502 may include additional lips extending inwardly from first and second lumens 506, 508 of sealing pack 502 to receive respective blades 150, 152 in a sealing relation.

In addition to the foregoing, sealing pack assembly 500 may be utilized in handheld powered surgical instruments. Reference may be made to U.S. Patent Application Publication No. 2015/0327850, the entire content of which is incorporated herein by reference, for a detailed discussed of the construction and operation of exemplary handheld powered surgical instruments. It is to be understood, therefore, that the disclosure is not limited to those precise embodiments, and that various other changes and modifications may be effected therein by one skilled in the art without departing from the scope or spirit of the disclosure.

What is claimed is:

1. An endoscopic stitching device comprising:
an elongate shaft assembly including an axial rod extending therethrough;
a tool assembly coupled with the elongate shaft assembly, the tool assembly including:
first and second jaws operatively coupled with the axial rod of the elongate shaft assembly such that axial displacement of the axial rod transitions the first and second jaws between open and closed positions; and
first and second needle receiving blades slidably disposed in the respective first and second jaws; and
a sealing pack disposed in the elongate shaft assembly to inhibit passage of fluid into the elongate shaft assembly, the sealing pack defining:
a central lumen configured to receive the axial rod therethrough, the central lumen including opposing planar portions and opposing arcuate portions, the opposing planar portions and opposing arcuate portions having a cross-section complementary to a cross-section of the axial rod; and
first and second lumens dimensioned to receive the respective first and second needle receiving blades therethrough, the first and second lumens being separate from the central lumen, the sealing pack including a body portion, a plurality of outer lips extending outwardly from the body portion, and a plurality of inner lips extending inwardly from the central lumen, each outer lip of the plurality of outer lips configured to engage the elongate shaft assembly in a sealing relation, each inner lip of the plurality of inner lips configured to engage the axial rod in a sealing relation.

2. The endoscopic stitching device according to claim 1, further comprising a plurality of sealing packs.

3. The endoscopic stitching device according to claim 2, wherein the plurality of sealing packs is formed as a single construct.

4. The endoscopic stitching device according to claim 1, wherein the axial rod includes opposing planar surfaces.

5. The endoscopic stitching device according to claim 4, wherein each inner lip of the plurality of inner lips includes planar surfaces configured to engage the respective opposing planar surfaces of the axial rod.

6. The endoscopic stitching device according to claim 1, wherein the elongate shaft assembly further includes a clevis including a base and a pair of legs, the base defining a central aperture in communication with the central lumen of the sealing pack.

7. The endoscopic stitching device according to claim 6, wherein the clevis defines third and fourth lumens in communication with the respective first and second lumens of the sealing pack.

8. The endoscopic stitching device according to claim 1, wherein the sealing pack is connected to the clevis.

9. The endoscopic stitching device according to claim 1, wherein the inner lips are spaced apart along a longitudinal axis defined by the elongate shaft assembly and are in registration with each other.

10. The endoscopic stitching device according to claim 1, wherein the opposing planar portions of the central lumen of the sealing pack are orthogonal to the first and second lumens.

11. The endoscopic stitching device according to claim 1, wherein the central lumen is interposed between the first and second lumens.

12. A tool assembly for use with an endoscopic stitching device, the tool assembly comprising:
   a support member;
   first and second jaws operatively coupled with the support member to transition between open and closed positions; and
   first and second needle receiving blades slidably received in the respective first and second jaws; and
   a sealing pack disposed within the support member to inhibit passage of fluid through the support member, the sealing pack defining:
      a central lumen configured to receive an axial rod therethrough, the central lumen including opposing planar portions and opposing arcuate portions; and
      first and second lumens dimensioned to receive the respective first and second needle receiving blades therethrough, the first and second lumens being separate from the central lumen, the sealing pack including a body portion, a plurality of outer lips extending outwardly from the body portion, and a plurality of inner lips extending inwardly from the central lumen, each outer lip of the plurality of outer lips configured to engage the support member in a sealing relation, each inner lip of the plurality of inner lips configured to engage the axial rod in a sealing relation.

13. The tool assembly according to claim 12, further comprising a plurality of sealing packs.

14. The tool assembly according to claim 13, wherein the plurality of sealing packs is formed as a single construct.

15. The tool assembly according to claim 12, wherein at least one inner lip of the plurality of inner lips includes planar surfaces configured to engage respective opposing planar surfaces of the axial rod.

16. The tool assembly according to claim 15, wherein at least one inner lip of the plurality of inner lips includes opposing arcuate surfaces.

17. The tool assembly according to claim 12, wherein the tool assembly further includes a clevis including a base and a pair of legs, the base defining a central aperture in communication with the central lumen of the sealing pack.

18. The tool assembly according to claim 17, wherein the clevis defines third and fourth lumens in communication with the respective first and second lumens of the sealing pack.

19. The tool assembly according to claim 17, wherein the sealing pack is connected to the clevis.

20. The tool assembly according to claim 17, wherein the inner lips are spaced apart along a longitudinal axis of the support member and are in registration with each other.

21. The tool assembly according to claim 17, wherein the outer lips are spaced apart along a longitudinal axis defined by the support member and are in registration with each other.

22. The tool assembly according to claim 12, wherein at least one outer lip of the plurality of outer lips is formed of a compressible material.

23. The tool assembly according to claim 12, wherein at least one inner lip of the plurality of inner lips and at least one outer lip of the plurality of outer lips are formed as a single construct.

* * * * *